United States Patent
Schulhofer et al.

(10) Patent No.: US 10,276,062 B2
(45) Date of Patent: *Apr. 30, 2019

(54) CALORIE OPTIMIZATION RESPIRATORY EXCHANGE FAT MACRO UTILIZATION METABOLIC PROFILE AND METHOD

(71) Applicant: Core Metabolics LLC, Santa Fe, NM (US)

(72) Inventors: Sanford David Schulhofer, Santa Fe, NM (US); Benjamin Stone, Vail, CO (US); David Dannenberg, Santa Fe, NM (US)

(73) Assignee: Core Metabolics LLC, Santa Fe, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/881,513

(22) Filed: Jan. 26, 2018

(65) Prior Publication Data
US 2018/0247566 A1 Aug. 30, 2018

Related U.S. Application Data

(63) Continuation-in-part of application No. 15/189,704, filed on Jun. 22, 2016.
(Continued)

(51) Int. Cl.
*A63F 9/24* (2006.01)
*G09B 19/00* (2006.01)
(Continued)

(52) U.S. Cl.
CPC ........ *G09B 19/0092* (2013.01); *A61B 5/0205* (2013.01); *A61B 5/024* (2013.01); *A61B 5/083* (2013.01)

(58) Field of Classification Search
CPC .................................................. G09B 19/0092
See application file for complete search history.

(56) References Cited

U.S. PATENT DOCUMENTS

| 4,909,259 A * | 3/1990 | Tehrani | A61B 5/083 600/483 |
| 6,475,158 B1 * | 11/2002 | Orr | A61B 5/024 600/529 |

(Continued)

*Primary Examiner* — Steve Rowland
(74) *Attorney, Agent, or Firm* — McGuire Woods LLP

(57) ABSTRACT

The disclosed embodiments include a calorie optimization respiratory exchange fat macro utilization metabolic system, comprising a computer-readable storage media having stored thereon computer-executable instructions; a processor for executing the computer-executable instructions, wherein the computer-executable instructions include instructions for receiving user profile data from a user, wherein the user profile data includes age, sex, height, weight, diet, fitness information; and if available, five specific metabolic data points from individual respiratory exchange testing; otherwise, calculating five specific metabolic points versus heart rate; generating an individualized metabolic profile for the user based on the five metabolic points; determining for the user an individualized target exercise heart rate zone as a percentage of maximum heart rate from the metabolic profile, and determining a nutritional guideline from the metabolic profile, measuring user compliance to facilitate machine learning progression and modification of the user metabolic profile, nutrition guideline, and target exercise heart rate zone.

22 Claims, 7 Drawing Sheets

Related U.S. Application Data

(60) Provisional application No. 62/184,766, filed on Jun. 25, 2015.

(51) Int. Cl.
*A61B 5/0205* (2006.01)
*A61B 5/024* (2006.01)
*A61B 5/083* (2006.01)

(56) References Cited

U.S. PATENT DOCUMENTS

| | | | |
|---|---|---|---|
| 2006/0031102 A1* | 2/2006 | Teller | A61B 5/411 |
| | | | 705/3 |
| 2006/0228681 A1* | 10/2006 | Clarke | A63B 24/00 |
| | | | 434/236 |
| 2006/0264730 A1* | 11/2006 | Stivoric | A61B 5/0205 |
| | | | 600/390 |
| 2007/0282176 A1* | 12/2007 | Shimada | G16H 40/63 |
| | | | 600/300 |
| 2014/0087336 A1* | 3/2014 | Wang | A61B 5/024 |
| | | | 434/127 |
| 2014/0213920 A1* | 7/2014 | Lee | A61B 5/222 |
| | | | 600/509 |
| 2014/0249379 A1* | 9/2014 | Proud | H04W 4/70 |
| | | | 600/301 |
| 2014/0330094 A1* | 11/2014 | Pacione | A61B 5/411 |
| | | | 600/301 |

\* cited by examiner

CALORIE OPTIMIZATION RESPIRATORY EXCHANGE FAT MACRO UTILIZATION METABOLIC PROFILE AND METHOD

BACKGROUND

The present disclosure generally relates to systems and methods to optimize respiratory exchange fat macro utilization metabolic profile.

Basal metabolic rate (BMR) refers to the energy (calories) required to maintain essential body functions and may account for 60 to 75% of daily total energy expenditure (TEE). BMR is in direct control of resting energy expenditure and ultimately determines whether an individual maintains, gains, or losses weight. Historical methods for estimating BMR have proven to be inaccurate with error rates ranging from 10 to 35%. Given that fact, the relative percentage of fat and carbohydrate constituting metabolic expenditure has been looked to as a more stable and reliable indicator of nutritional status. Fat and carbohydrate calories (commonly referred to as macronutrients) contribute independently to metabolic demand and that value is expressed as the Respiratory Exchange Ratio (RER) and is most often derived from laboratory indirect calorimetry metabolic testing, wherein oxygen and carbon dioxide gases from inspiration and expiration are collected and measured as a function of heart rate from rest through anaerobic threshold. An RER value of 1.0 equals 100% carbohydrate energy utilization and an RER of 0.7 equals 100% fat energy utilization. Metabolic testing is a critical tool for the accurate measurement of individual metabolism in the medical, nutrition and fitness industries, yet it is expensive and has limited availability to the general population, and consequently, testing utility is not widely available. Also, calculating accurate BMR and energy expenditures associated with typical activities of daily living from indirect calorimetry is challenging as a result of hardware limitations. More accurate measurements require a complex sealed and airtight free-living laboratory setting (bomb or direct calorimetry) wherein all respiratory gasses are constantly measured over a 24-hour period and all sources of caloric intake are strictly measured. Ideally, an individual would have an RER value below 0.85 and approaching 0.7 at rest, during the course of routine activities, and with low intensity exercise, wherein fat is the optimal and primary energy source. However, the macronutrient composition of an individuals diet (relative fat % and carbohydrate %), and timing of meals is critical to determining whether an RER value is higher or lower at rest, or with low intensity activity. Low fat diets and frequent ingestion of carbohydrate are associated with a higher fasting and 24-hour glucose and consequently, a higher resting and low intensity activity RER. Alternatively, a high fat diet and relative periods of fasting greater than 2 hours, are associated with a lower fasting and 24-hour glucose and consequently, a lower resting and low intensity activity RER. Thus, increasing an individual's dietary fat macro utilization (FMU) will increase their resting fat use (RFU), and this is quantitated by a lower RER. Additionally, the diet and fitness industries have long desired to improve an individuals fat burning during exercise and have published target exercise heart rate zones for maximizing fat burning that are either 60 to 70% of an individuals maximum heart rate (estimated by the 220-age formula), or derived from the Karnoven method, wherein target heart rate equals ((maximum heart rate−resting heart rate)×% intensity)+resting heart rate. Unfortunately, neither of these methods is accurate, especially when compared to an individual's actual RER test (100% accurate) or the CORE FMU estimations (Root Mean Square Error beats per sec: Karnoven 33.83, Traditional 23.71, CORE FMU method 17.57).

BRIEF SUMMARY OF THE DISCLOSED EMBODIMENTS

The disclosed embodiments provide encrypted data retrieval systems and methods to provide access to encrypted data. In accordance with one embodiment, a novel calorie optimization respiratory, exchange (CORE) fat macro utilization (FMU) metabolic profile system and method is provided. The disclosed system and method provide an alternative, yet functionally equivalent outcome, to indirect calorimetry (respiratory exchange) testing in a cost effective manner with horizontal and vertical scalability to the general population, with wearable device data integration; for improved fat macro utilization at with activities of daily living, and with low intensity exercise; more accurate target exercise heart rate zones; and real-time determination of the number of minutes necessary to achieve a daily fat burning goal.

In accordance with another illustrative embodiment, a CORE FMU system and method are designed to run in the background of a website or mobile app, thereby allowing a user to enter their biometric data into the CORE FMU system for the determination of their individual metabolic profile and the establishment of their baseline nutritional status (percent of fat and carbohydrate kcal/min relative to heart rate), fitness (individualized target heart exercise zone to optimize fat macro utilization (FMU), and diet planning. In certain embodiments, the CORE FMU system may be configured to automatically receive the biometric data of a user from one or more biometric devices such as, but not limited to, a heart rate monitor, a heart rate enabled device, and/or an accelerometer enabled device. These devices may be wearable, (e.g. smartwatch such as ☐ Watch™ or Fit-Bit™), mobile (e.g. a smartphone such as ☐ iPhone™ with an integrated accelerometer, heart rate monitor and/or GPS), or stationary.

In accordance with a further illustrative embodiment, the CORE FMU system is configured to allow a user to enter data collected directly from personal respiratory exchange testing that they may have previously performed. The profile may be associated with a wearable heart rate or accelerometer-enabled wearable device for the conversion of estimated kilocalorie expense into fat and carbohydrate kilocalorie expense based upon the wearable device. In some embodiments, the system is also utilized in conjunction with a calorie restriction equation, basal metabolic rate and energy expenditure estimations to assist the user in designing and implementing weight loss, maintenance, and exercise programs.

In accordance with a further illustrative embodiment, the CORE FMU system is configured to allow a user to enter data collected directly from personal respiratory exchange testing that they may have previously performed. The profile may be associated with a wearable heart rate or accelerometer-enabled wearable device for the conversion of estimated kilocalorie expense into fat and carbohydrate kilocalorie expense based upon the wearable device. In some embodiments, the system is also utilized in conjunction with a calorie restriction equation, basal metabolic rate and energy expenditure estimations to assist the user in designing and implementing weight loss, maintenance, and exercise programs.

In accordance with a further illustrative embodiment, a system comprising a computer-readable storage media having stored therein computer-executable instructions; and a processor for executing the computer-executable instructions is provided. The computer-executable instructions include instructions for: receiving user profile data of a user; determining metabolic points (kcals/min) versus heart rate (beats/min); generating an individualized metabolic profile for the user; determining an individualized target exercise heart rate zone as a percentage of maximum heart rate from the metabolic profile to optimize fat macro utilization; and determining real-time, the number of minutes of activity still necessary to achieve the daily fat burning goal.

In accordance with a further illustrative embodiment, a system comprising a computer-readable storage media having stored therein computer-executable instructions; and a processor for executing the computer-executable instructions is provided. The computer-executable instructions include instructions for: receiving user profile data from a user, wherein the user profile data includes, age, sex, height, weight, diet, and fitness information; and optionally five metabolic points from personal respiratory exchange testing, determining the five metabolic points (kcals/min) versus heart rate (beats/min); generating an individualized metabolic profile for the user; determining an individualized target exercise heart rate zone as a percentage of maximum heart rate from the metabolic profile; and determining for the user an individualized nutritional plan by percent fat, percent carbohydrate and percent protein to optimize fat macro utilization at rest, with activities of daily living and endurance exercise for weight loss, maintenance, and endurance exercise enhancement from the metabolic profile.

Additional details of the disclosed embodiments are provided below in the detailed description and corresponding drawings.

BRIEF DESCRIPTION OF THE DRAWINGS

Illustrative embodiments of the present invention are described in detail below with reference to the attached drawing Figures, which are incorporated by reference herein, and wherein.

Figure 1:
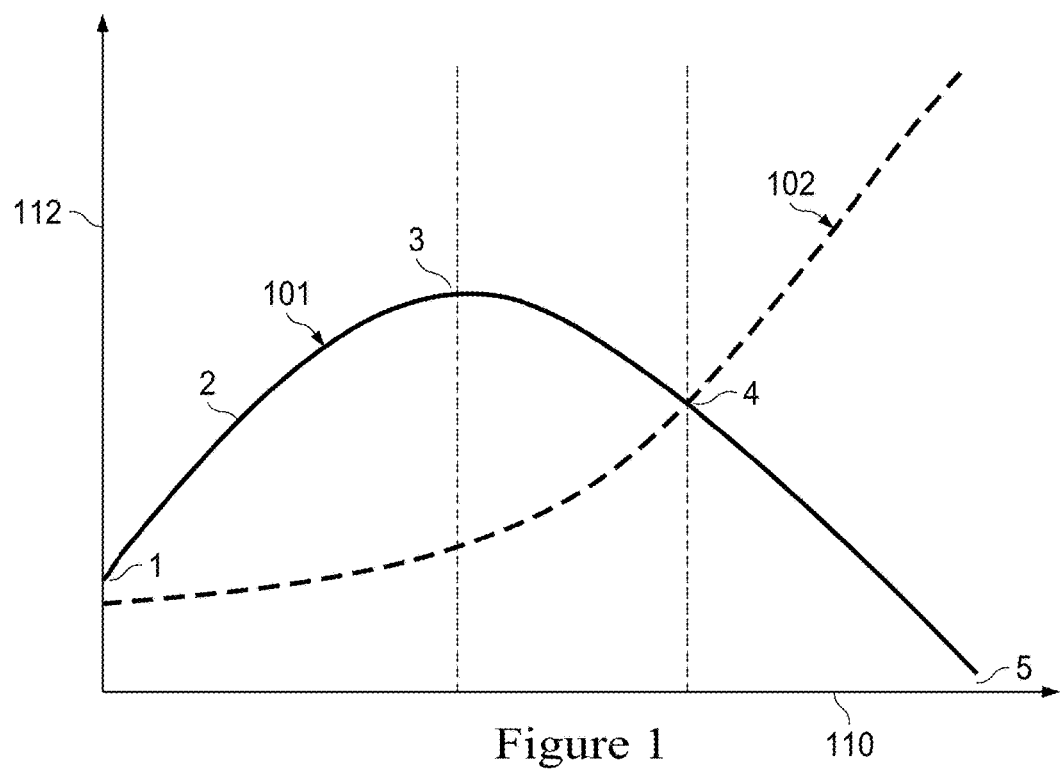
FIG. 1 is a mathematical model depicting respiratory exchange ratio substrate utilization (kcal/min vs. heart rate), corresponding to five critical points associated with fat and carbohydrate metabolism in accordance with an embodiment.
Figure 2:
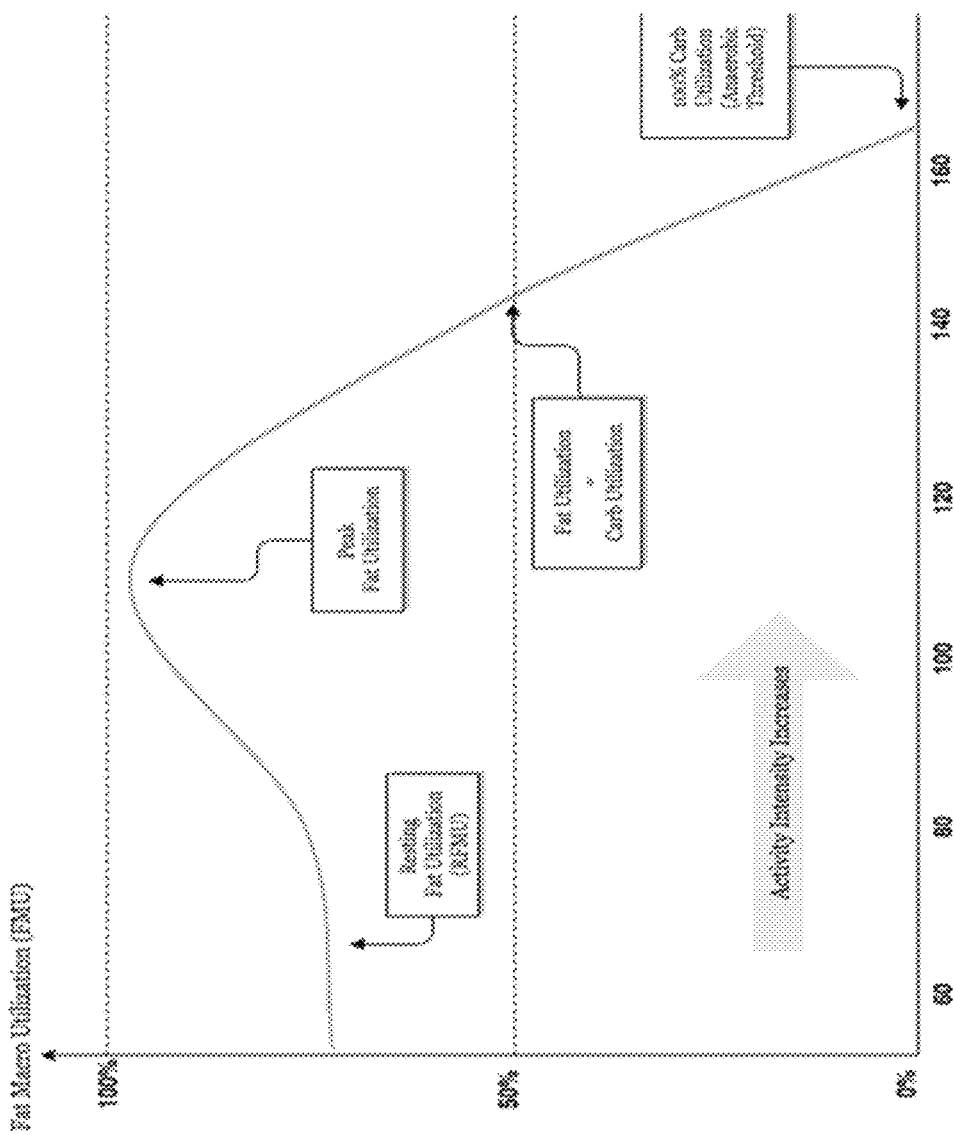
FIG. 2 is a mathematical model depicting respiratory exchange ratio substrate utilization (fat macro utilization or FMU (y-axis) vs. heart rate (x-axis)), relative to a range of activity levels that incorporates the five critical points associated with fat metabolism in accordance with an embodiment.
Figure 3:
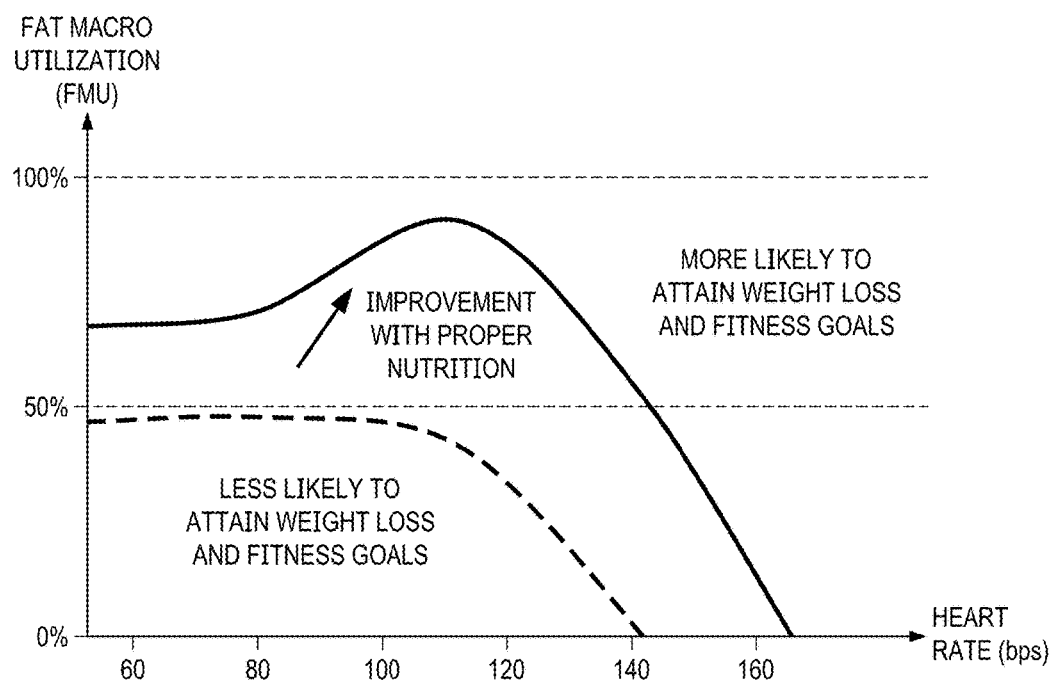
FIG. 3 is a mathematical model depicting fat utilization ratios wherein individual fat macro utilization (y-axis) vs. heart rate (x-axis) profiles differ between individuals. The "red line" indicates an individual with poor resting fat use (RFU) that will trend towards the "blue" improved RFU with compliance to the CORE FMU system and method nutritional recommendations over time in accordance with an embodiment.

The illustrated figures are only exemplary and are not intended to assert or imply any limitations with regard to the environment, architecture, design, or process in which different embodiments may be implemented. The illustrated figures are only exemplary and are not intended to assert or imply any limitation with regard to the environment, architecture, design, or process in which different embodiments may be implemented.

DETAILED DESCRIPTION

The invention and the various features and advantageous details thereof are explained more fully with reference to the non-limiting embodiments that are illustrated in the accompanying drawings and detailed in the following description. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, descriptions of well-known materials, processing techniques, components and equipment are omitted so as not to unnecessarily obscure the invention in detail. It should be understood, however, that the detailed description and the specific examples, while indicating particular embodiments of the invention, are given by way of illustration only and not by way of limitation. Further, the illustrated figures are only exemplary and are not intended to assert or imply any limitation with regard to the environment, architecture, design, or process in which different embodiments may be implemented. Various substitutions, modifications, additions, and/or rearrangements within the spirit and/or scope of the underlying inventive concept will become apparent to those skilled in the art and from this disclosure.

Other features and advantages of the disclosed embodiments will be or will become apparent to one of ordinary skill in the art upon examination of the following figures and detailed description. It is intended that all such additional features and advantages be included within the scope of the disclosed embodiments.

As used within the written disclosure and in the claims, the terms "including" and "comprising" are used in an open-ended fashion, and thus should be interpreted to mean "including, but not limited to". Unless, otherwise indicated, as used throughout this document, "or" does not require mutual exclusivity. In addition, as used herein, the singular forms "a", "an", and "the" are intended to include the plural forms as well, unless the context clearly indicates otherwise.

The disclosed embodiments include systems, methods, and computer program products for performing a calorie optimization respiratory exchange (CORE) fat macro utilization (FMU) metabolic determination and generating an individualized metabolic profile for each user. In some embodiments, the CORE FMU system is also configured to determine an individualized target exercise heart rate profile as a percentage of maximum heart rate from the metabolic profile and/or determining for the user a unique nutritional guideline from the metabolic profile with activity minutes necessary to achieve fat burning goals.

The disclosed embodiments are based on the analysis of respiratory exchange tests performed on individuals of varied adult ages, socioeconomic backgrounds, general health status, and fitness over the course of many years. The results of the tests were compiled and regressively analyzed to determine a statistically significant mathematical model of an individual's fat and carbohydrate metabolism relative to heart rate.

As an example, FIG. 1 is a graph of a mathematical model depicting substrate utilization from an indirect calorimetry respiratory exchange ratio test (kcals/min vs. heart rate) corresponding to five critical points associated with fat and carbohydrate metabolism in accordance with an embodiment. In the depicted embodiment, the x-axis 110 represents heart rate (beats/min) and the y-axis 112 represents calorie expenditure (kcals/min). Curve 101 represents fat metabolism versus heart rate. Curve 102 represents carbohydrate metabolism versus heart rate.

Figure 4:
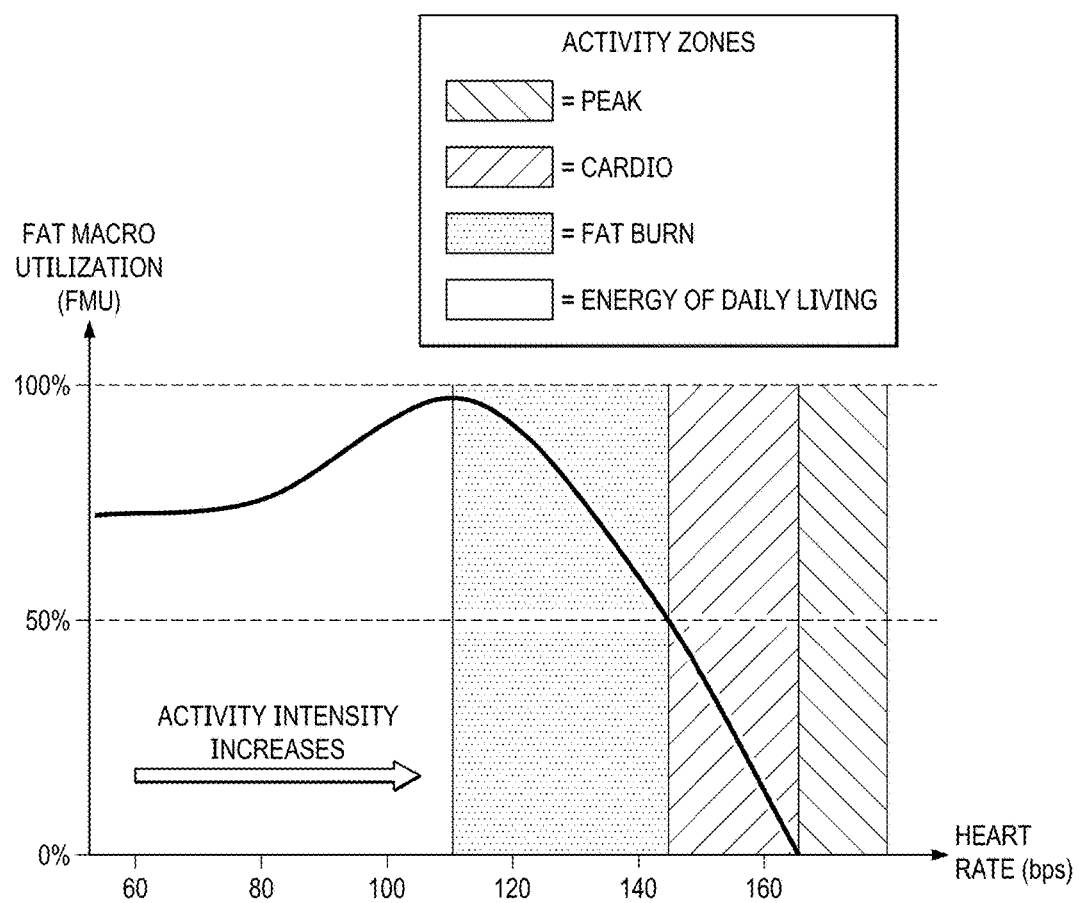
FIG. 4 is a mathematical model depicting clear individual activity zones based upon the five metabolic points as a function of fat macro utilization (y-axis) vs. heart rate (x-axis) profiles with an embodiment.

In one embodiment, using the mathematical model in FIG. 1 that represents substrate utilization (kcal/min vs. heart rate), five critical points: a resting fat use point 1, an energy of daily living use point 2, a peak fat use point 3, a metabolic equivalency point 4, and a carbohydrate dependency point 5 that are associated with fat and carbohydrate metabolism are determined. In one embodiment, the resting fat use point 1 is equal to the proportional fat:carbohydrate ratio calculated from the energy of daily living use point 2. In one embodiment, the target exercise heart rate zone is determined to be between the peak fat use point 3 and the metabolic equivalency point 4 as illustrated in FIGS. 1 and 4.

In one embodiment, further analysis required evaluating the biometric variables of the tested individuals and quantifying the relative significance of each of these variables, for each of the five points, of their metabolic curve. For example, in one embodiment, the following variable relative weights are assigned to each of the five points:

Points 1 and 2 (fat usage): 80% nutrition, 10% age, 10% exercise volume.

Point 3 (fat usage): 50% nutrition, 20% age, 30% exercise volume.

Point 3 (% maximum heart rate): 40% nutrition, 10% age, 50% exercise volume.

Point 4 (% maximum heart rate): 40% nutrition, 10% age, 40% exercise volume, 10% BMI.

Point 5 (% maximum heart rate): 50% exercise volume, 40% age, 10% BMI.

In one embodiment, the CORE FMU system accounts for a user's biometric data in a user profile. For example, in one embodiment, the biometric data of a user includes age (years), height (centimeters or inches), weight (kilograms or pounds), diet (% macronutrients), and exercise volume of the individuals.

Based upon the above analysis, the system is configured to determine the proportional value of each of these variables relative to their metabolic contribution to each of the five points. In one embodiment, a widely disseminated formula (220–age) is used for the estimation of maximum heart rate. As stated above, the 5 critical metabolic points for fat and carbohydrate (kcals/min) vs. heart rate (beats/min) are described as follows:

point (1) resting fat use (RFU),
point (2) energy of daily living (EDL),
point (3) peak fat use (PFU),
point (4) metabolic equivalency point (MEP),
point (5) carbohydrate dependency (CD—zero fat burn).

Figure 5:
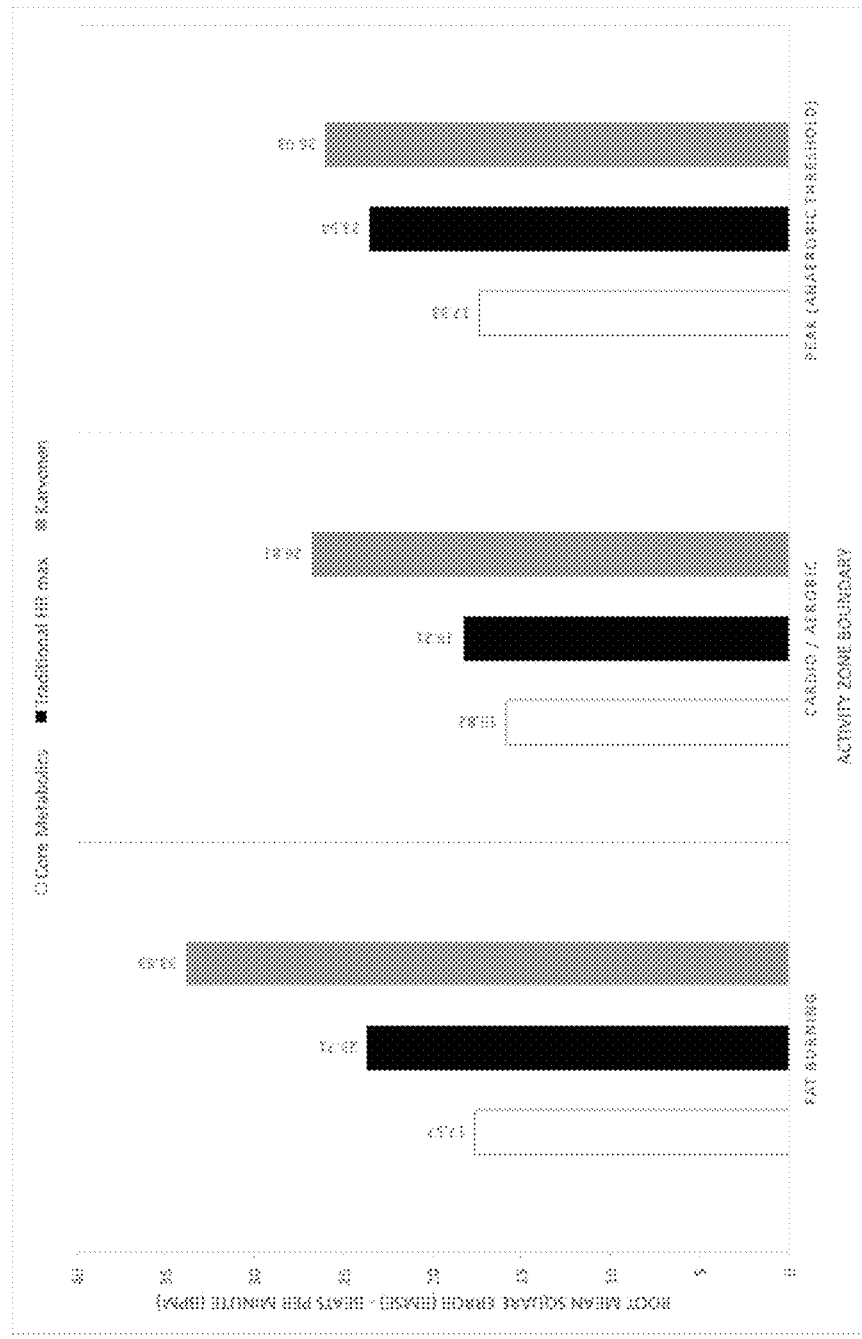
FIG. 5 is a graph illustrating a comparison of RMSE (root mean square error) in predicted vs. observed Activity Zone boundaries that incorporate five critical metabolic points using 3 methods wherein the CORE FMU system and method accuracy is notably improved with an embodiment.

FIG. 5 illustrates the higher comparative accuracy of the CORE FMU target heart rate exercise zone estimations against the health/exercise industry standards. An actual metabolic test RER profile is the gold standard for metabolic processes. An exercise effort at PFU represents a maximal fat burning rate at a specific heart rate and is associated with high rates of adipose and intramuscular triglyceride utilization. Exercise efforts just below or above PFU provides a range of fat burning that may seem equal; however, it has been shown that exercise efforts between PFU and MEP is the desired exercise effort necessary to not simply burn fat calories, but to 1) selectively increase the ratio of fat calories obtained from intramuscular triglyceride stores and 2) to provide the metabolic enzymatic stress on the fat burning machinery of the muscle cell necessary to up-regulate the fat burning system and consequently shift the metabolic curve to the right. A right shift of the curve translates to not only increased fat burning at rest and lower heart rate activities, but to higher power outputs (hence speed) at a given exercise effort with less glycogen depletion. This is critically important to weight loss and exercise endurance and the mechanism that allows a user to optimize their fat burning capabilities. Additionally, utilization of intramuscular triglycerides leads to increased post-exercise oxygen consumption and additional adipose utilization to replace burned fat and glycogen muscle stores. The nutrition and fitness industries have been espousing heart rate zones that are essentially derived from a maximal heart rate and simply encourage lower heart rate zones with the intention of encouraging fat metabolism. Yet, without a metabolic test, a given person has no way of knowing what heart rates may be associated with fat burning. In fact many people have inverted metabolic profiles and fail to burn fat at essentially any heart rate over their resting rate. Thus, these standards lack any scientific rigor. The CORE FMU estimations are derived from metabolic tests and as the chart illustrates provide a much sounder methodology, lower error rate (RMSE), and optimize fat burning in a far more profound manner. In addition, when coupled with the CORE nutrition plans, fat burning at rest and with exercise is further optimized.

Figure 6:
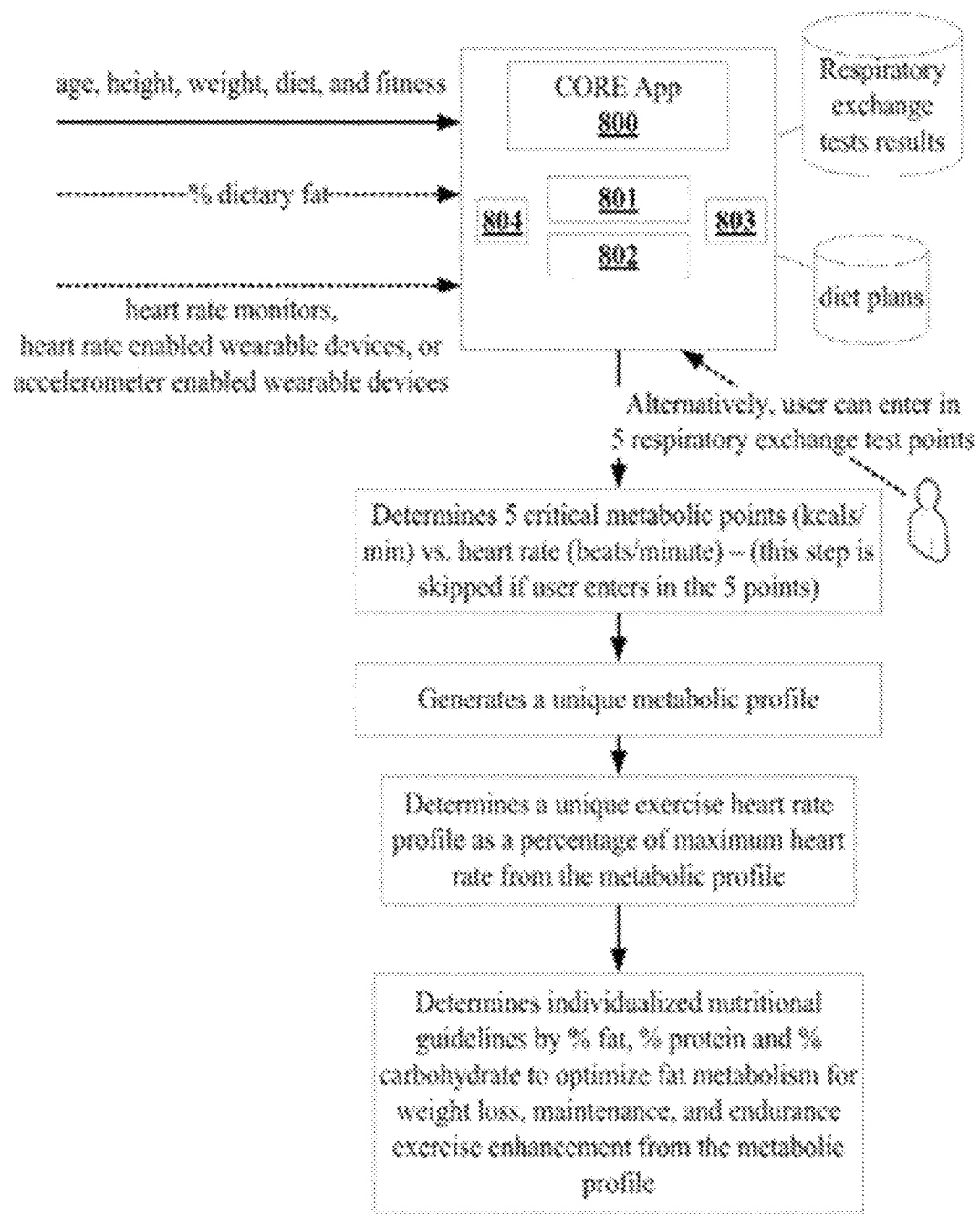
FIG. 6 is a high level block diagram illustrating a calorie optimization respiratory exchange fat macro utilization metabolic system in accordance with one embodiment.

FIG. 6 is a high level block diagram illustrating an embodiment of a CORE FMU application 800. As depicted in the example embodiment, the CORE FMU application 800 may be implemented in a mobile application that is installed on a user device such as but not limited to a mobile device, a smart watch, laptop, tablet, or other computing device. Alternatively, the CORE FMU application 800 may be implemented as a web application accessible to the user through the Internet or other communication networks. In this embodiment, the web application interface may be hosted by a Web-server, whereas the computer-executable instructions associated with the CORE FMU application 800 may be executed on one or more backend servers. As understood by one of ordinary skill in the art, each of these computing devices contain memory 801 (volatile and/or nonvolatile memory) and one or more processors 802 for storing and executing the instructions associated with the CORE FMU metabolic system. In addition, each of these computing devices include a networking component or networking interface 803 that enables the devices to communicate with other devices over a network such as, but not limited to, the Internet. The system executing the CORE FMU application is referred to herein as the CORE FMU metabolic system. In one environment, the CORE FMU metabolic system communicates with one or more databases for retrieving respiratory exchange test results or dietary plan information. The CORE FMU metabolic system also includes input/output interfaces 804 for receiving data such as a keyboard, mouse, built-in buttons, heart rate monitor, and/or a touch screen display.

In one embodiment, the CORE FMU metabolic system receives age, height, weight, diet, and fitness information for a particular user. In certain embodiments, the CORE FMU metabolic system may also receive percentage of dietary fat information for the user. Still, in another embodiment, the CORE FMU metabolic system is configured to enable a user to enter the data from outside respiratory exchange tests directly into the 5 points of the CORE FMU metabolic system in order to generate their metabolic profile and access the additional functions.

Alternatively, in some embodiments, the CORE FMU metabolic system is configured to receive data from heart rate monitors, heart rate enabled wearable devices, or accelerometer enabled wearable devices associated with the user. For example, while not necessary for minimal functional use, the CORE FMU metabolic profile provides exceptional utility and value when used in conjunction with heart rate monitors, heart rate enabled wearable devices, or accelerator enabled wearable devices that estimate kilocalorie expenditure with activity, to convert daily kcal energy expenditure into fat and carbohydrate kcal expenditure. With certain wearable heart rate enabled devices this may be a real-time measurement (fat and carbohydrate kcal/min), with others a conversion of daily kcal values according to API reporting parameters.

The CORE FMU metabolic system then determines an individualized target exercise heart rate profile (ranging from point 3 to point 4) for each user, as percentage of maximum heart rate, from the CORE FMU metabolic profile, to illustrate an optimal target exercise heart rate zone for peak fat metabolism (FIGS. 1 and 4). Further, in some embodiments, compliance measurements with the nutritional recommendations facilitates the machine learning process for progression and modification of the user's metabolic profile, including diet recommendations, and adjusted target exercise heart rate zones. The profile may be combined with calorie restriction weight loss programs based upon basal metabolic rate and total estimated energy requirements to determine and monitor resting, energy of daily living, and exercise fat metabolism for optimal nutrition planning. Moreover, in some embodiments, the total number of daily activity minutes necessary to achieve the daily fat burning goal are determined, progressively monitored and modified real-time to allow the user to see how many minutes of activity are necessary to reach their goal.

The CORE FMU system metabolic outcomes are used to determine individualized nutritional guidelines of % fat, % carbohydrate and % protein to optimize fat metabolism for weight loss, maintenance, and maximizing endurance exercise performance. In one embodiment, the CORE FMU system subsequently updates the database of macronutrients with customized and progressively modified diet plans consistent with metabolic changes over time.

Figure 7:
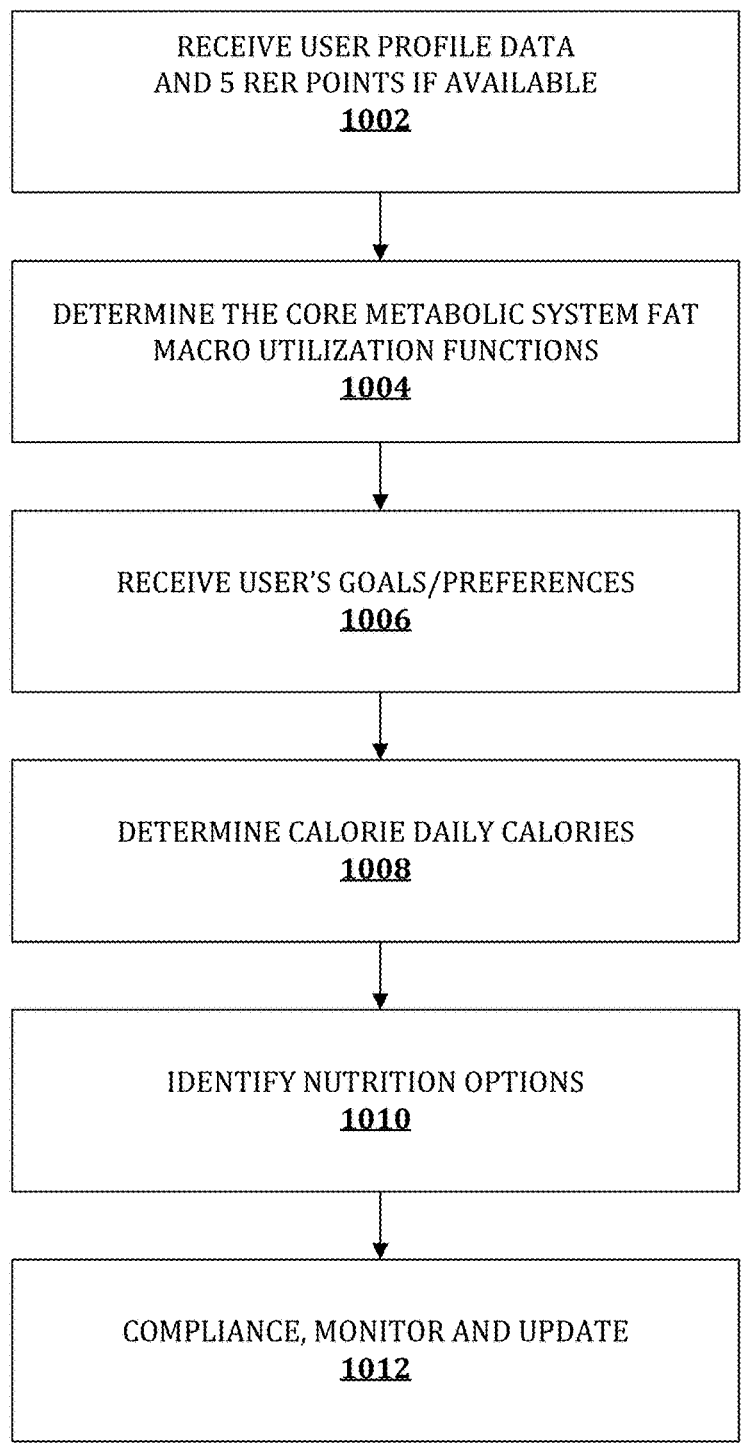
FIG. 7 illustrates an example algorithm or process executed by the calorie optimization respiratory exchange fat macro utilization metabolic system in accordance with one embodiment.

FIG. 7 illustrates an example algorithm or process 1000 executed by the calorie optimization respiratory exchange metabolic system in accordance with one embodiment. The process begins at step 1002 by receiving user profile data. As described above, the profile data may be received through the user input or directly by communicating with one or more devices or systems. In one embodiment, the user profile data includes age, sex, height, weight, exercise volume (scale 1 to 5) and nutritional status value (for example, 1=10% fat, 2=20% fat, 3=30% fat, and 4=40% fat diet). In some embodiments, the process may be configured to optionally receive the 5 points of data from a personal respiratory exchange test.

At step 1004, the process is configured to determine the CORE FMU metabolic system functions including determining the maximum heart rate, resting metabolic rate, nutrition status, metabolic points, target exercise fat metabolism zone, macronutrient profile for future diet guidelines, and daily total estimated energy expenditure. As an example, in one embodiment, the process performs the following calculations:

Calculate maximum heart rate: 220−age

Calculate resting metabolic rate (RMR): Miflin–St. Joer model (kcal/day)

Male: 9.99×weight (kg)+6.25×height (cm)−4.92×age (yrs)+5

Female: 9.99×weight (kg)+6.25×height (cm)−4.92×age (yrs)−16

Calculate Nutrition Status

Calculate metabolic points 1-5:

Point 1: Resting Fat Use (RFU) kcal/min: Point 2 RER proportional extrapolation applied to kcal/min data from wearable or BMR/TEE estimation equations Point 2: Energy of Daily Living Use (EDL): Fat kcal/min ((nutrition 80%)+(age 10%)+(exercise volume 10%))

Point 3: Peak Fat Use (PFU): kcal/min ((nutrition 50%)+(age 20%)+(exercise volume 30%))

Point 3: % Maximum heart rate: beats/min ((nutrition 40%)+(age 10%)+(exercise volume 50%)

Point 4: Mean Equivalency Point (MEP): % Maximum heart rate: beats/min ((nutrition 40%)+(age 10%)+(exercise volume 40%)+(BMI 10%))

Point 5: Carbohydrate Dependency (CD): % Maximum heart rate: beats/min ((exercise volume 50%)+(age 40%)+(BMI 10%))

Calculate User target Fat Metabolism Exercise Zone: (% Maximum heart rate and BPM): Range from point 3 to point 4.

Calculate Macronutrient profile for future diet guideline.

Calculate daily Estimated Energy Expenditure (EEE).

Data comes from the CORE FMU system metabolic profiles and incorporates wearable heart rate data or step counts to recalculate kcal/min into fat and carbohydrate kcal/min for resting (point 1), energy of daily living (point 2), and exercise.

Calculate Daily Total Estimated Energy (TEE) expenditure.

Data comes from adding the RMR and RER kcal/min.

Formulates charts for calories burned (fat and carbohydrate utilization) for resting, energy of daily living, exercise and total by day, week and month.

Formulates charts for steps taken with energy of daily living, exercise and total by day, week and month.

An example calculation is shown below:

Example: 50 year old male, 177.8 cm, 64 kg

Maximum heart rate: 220−50=170

RMR: Miflin St. Joer=1510 kcal/day

Point 1: RER fat:carbohydrate ratio from point 2 (kcal/min)=1.25:1 applied to FitBit™ data reporting at 1.2 kcal/min=0.75 kcal/min fat and 0.45 kcal/min carbohydrate Point 2: ((3.9 kcal/min×80%)+(3.1 kcal/min×10%)+(3.5 kcal/min×10%))=226.8 kcal/hour of EDL fat burn Point 3: ((4.3×50%)+(4.7×20%)+(4.1×30%))=4.30 kcal/min=258 kcal/hr of PF fat burn Point 3: ((43×40%)+(47×50%)+(20×10%))=42.95% Maximum heart rate=73 BPM for PF Point 4: ((42×40%)+(60×10%)+(70×40%)+(20×10%))=64.8% % Maximum heart rate=110 BPM Point 5: ((84×50%)+(69×40%)+(20×10%))=71.6% Maximum heart rate=123 BPM Target Exercise Fat Burn Zone: (42.95% to 64.8% and 73 to 110 BPM)

Macronutrient profile: Fat 40%, Carbohydrate 28%, Protein 32%

Referring back to FIG. 7, at step 1006, the process receives the user's goals and preferences. For example, in one embodiment, the process receives the user's weight loss goal (e.g. the amount of weight desired to lose and over what period of time) and food preferences and/or food allergy restrictions.

At step 1008, the process determines the amount of user calories to lose/day over the given period of time. At step 1010, the process identifies and presents nutrition options from the customized food database for the user to develop a personalized diet based upon system nutrition percentages and user weight loss goals.

At step 1012, the process monitors and updates the user's progress based on the user's documented compliance with calorie intake and biometric changes. For example, in one embodiment, the process determines the amount of user daily calories in and out and charts the user's progress daily, weekly and monthly relative to goal. Further, in another embodiment, the process displays the number of activity minutes that remain for the user to meet their fat calorie burn goal for the day. Additionally, in one embodiment, the process is configured to receive periodic updated biometric changes as prompted by the system, or as needed. For example, in one embodiment, the process periodically updates the user metabolic profile, heart rate profile, nutrition percentages, and diet options, based upon confirmed nutrition compliance.

As previously stated, the above descriptions, including the diagrams are intended merely as examples of the disclosed embodiments and is not intended to limit the structure, process, or implementations of the disclosed embodiments. As understood by one of ordinary skill in this art that certain aspects of the disclosed embodiments described herein may be implemented as firmware, firmware/software combination, firmware/hardware combination, or a hardware/firmware/software combination.

It is further understood that various modifications may be made therein and that the subject matter disclosed herein may be implemented in various forms and examples, and that the teachings may be applied in numerous applications, only some of which have been described herein. It is intended by the following claims to claim any and all applications, modifications, and variations that fall within the true scope of the present teachings.

The above-disclosed embodiments have been presented for purposes of illustration and to enable one of ordinary skill in the art to practice the disclosure, but the disclosure is not intended to be exhaustive or limited to the forms disclosed. Many insubstantial modifications and variations will be apparent to those of ordinary skill in the art without departing from the scope and spirit of the disclosure. The scope of the claims is intended to broadly cover the disclosed embodiments and any such modification.

The above-disclosed embodiments have been presented for purposes of illustration and to enable one of ordinary skill in the art to practice the disclosed embodiments, but are not intended to be exhaustive or limited to the forms disclosed. Many insubstantial modifications and variations will be apparent to those of ordinary skill in the art without departing from the scope and spirit of the disclosure. For instance, although the flowcharts depict a serial process, some of the steps/blocks may be performed in parallel or out of sequence, or combined into a single step/block. The scope of the claims is intended to broadly cover the disclosed embodiments and any such modification.

As used herein, the singular forms "a", "an" and "the" are intended to include the plural forms as well, unless the context clearly indicates otherwise. It will be further understood that the terms "comprise" and/or "comprising," when used in this specification and/or in the claims, specify the presence of stated features, steps, operations, elements, and/or components, but do not preclude the presence or addition of one or more other features, steps, operations, elements, components, and/or groups thereof. In addition, the steps and components described in the above embodiments and figures are merely illustrative and do not imply that any particular step or component is a requirement of a claimed embodiment.

We claim:

1. A calorie optimization respiratory exchange fat macro utilization metabolic system comprising:
    a computer-readable storage media having stored thereon computer-executable instructions; and
    a processor for executing the computer-executable instructions, wherein the computer-executable instructions include instructions for:
    receiving user profile data of a user, wherein the user profile data comprises age, sex, height, weight, nutrition status, and fitness information;
    determining five metabolic points versus heart rate;
    generating an individualized metabolic profile for the user based on the five metabolic points;
    determining for the user, an individualized nutritional guideline from the metabolic profile, wherein the individualized nutritional guideline is determined based on percent fat, percent carbohydrate, and percent protein to optimize fat metabolism and increase resting fat use for weight loss, maintenance, and endurance exercise enhancement; and
    determining an individualized target exercise heart rate zone as a percentage of maximum heart rate from the metabolic profile;
    wherein determining the five metabolic points versus heart rate is in response to receiving the metabolic points as input from a respiratory exchange test;
    wherein the target exercise heart rate zone is determined to be between a peak fat use point and a metabolic equivalency point.

2. The calorie optimization respiratory exchange fat macro utilization metabolic system of claim 1, wherein the computer-executable instructions include instructions for determining for the user, an individualized nutritional guideline from the metabolic profile.

3. The calorie optimization respiratory exchange fat macro utilization metabolic system of claim 2, wherein the user profile data includes age, sex, height, weight, nutritional status, and fitness information.

4. The calorie optimization respiratory exchange fax macro utilization metabolic system of claim 3, further comprising determining the metabolic points versus heart rate in response to receiving the metabolic points as user input from a user respiratory exchange test.

5. The calorie optimization respiratory exchange fat macro utilization metabolic system of claim 4, wherein there are five metabolic points.

6. The calorie optimization respiratory exchange fat macro utilization metabolic system of claim 5, wherein the individualized nutritional guideline is determined by percent fat, percent carbohydrate and percent protein to optimize fat metabolism at rest, with activities of daily living, and endurance exercise for weight loss, maintenance, and endurance exercise enhancement.

7. The calorie optimization respiratory exchange fat macro utilization metabolic system of claim 6, wherein measuring user compliance is performed to progress and modify individualized nutritional guidelines of the user, activity minutes to achieve daily fat burn goal and metabolic profile.

8. The calorie optimization respiratory exchange fat macro utilization metabolic system of claim 5, wherein the five metabolic points are a resting fat use point, an energy of daily living fat use point, a peak fat use point, a metabolic equivalency point, and a carbohydrate dependency point.

9. The calorie optimization respiratory exchange fat macro utilization metabolic system of claim 8, wherein the resting fat use point is a ratio of fat:carbohydrate determined from a respiratory exchange ratio testing of the energy of daily living point.

10. The calorie optimization respiratory exchange fat macro utilization metabolic system of claim 9, wherein a total kcals/min at at least one of the resting fat use point and the energy of daily living fat use point are derived from at least one of a Miflin St. Joer and a user's wearable data reporting.

11. The calorie optimization respiratory exchange fat macro utilization metabolic system of claim 5, wherein measuring user compliance is performed to progress and modify target exercise heart rate zone of the user.

12. The calorie optimization respiratory exchange fat macro utilization metabolic system of claim 3, wherein the diet information includes an average percentage of daily fat intake.

13. The calorie optimization respiratory exchange fax macro utilization metabolic system of claim 3, wherein the fitness information includes a resting heart rate.

14. The calorie optimization respiratory exchange fat macro utilization metabolic system of claim 1, wherein the computer-executable instructions include instructions for generating a web-based user interface for receiving data from the user of the Internet.

15. A computer-implemented method comprising:
receiving user profile data of a user;
determining metabolic points versus heart rate;
generating an individualized metabolic profile for the user; and
generating an individualized target exercise heart rate profile as a percentage of maximum heart rate from the metabolic profile;
wherein determining the metabolic points versus heart rate is in response to receiving the metabolic points as input from a respiratory exchange test;
wherein a target exercise heart rate profile is determined to be between a peak fat use point and a metabolic equivalency point.

16. The computer-implemented method of claim 15, further comprising determining for the user an individualized nutritional guideline from the metabolic profile.

17. The computer-implemented method of claim 16, wherein the user profile data includes age, sex, height, weight, nutritional status, and fitness information.

18. The computer-implemented method of claim 17, wherein further comprising determining the metabolic points versus heart rate in response to receiving the metabolic points as user input, the metabolic points determined from a user respiratory exchange test.

19. The computer-implemented method of claim 18, wherein there are five metabolic points.

20. The computer-implemented method of claim 19, wherein the individualized nutritional guideline is determined by percent fat, percent carbohydrate, and percent protein to optimize fat metabolism at rest, with activities of daily living and endurance exercise for weight loss, maintenance, and endurance exercise enhancement.

21. The computer-implemented method of claim 20, further comprising generating a web-based user interface for receiving data from the user of the Internet.

22. A non-transitory machine-readable medium comprising instructions stored therein, which when executed by one or more processors, causes the one or more processors to perform operations comprising:
receiving user profile data of a user, wherein the user profile data includes age, sex, height, weight, nutritional status, and fitness information;
determining metabolic points versus heart rate;
generating an individualized metabolic profile for the user; and
generating an individualized target exercise heart rate profile as a percentage of maximum heart rate from the metabolic profile;
wherein determining the metabolic points versus heart rate is in response to receiving the metabolic points as input from a respiratory exchange test;
wherein a target exercise heart rate profile is determined to be between a peak fat use point and a metabolic equivalency point.

\* \* \* \* \*